United States Patent [19]

Rich

[11] Patent Number: 4,572,185
[45] Date of Patent: Feb. 25, 1986

[54] NONPLANAR SURGICAL NEEDLE HOLDER AND RELATED SUTURING METHOD

[76] Inventor: Mark Rich, 111-56 76 Dr., Apt. C2, Forest Hills, N.Y. 11375

[21] Appl. No.: 582,835

[22] Filed: Feb. 23, 1984

[51] Int. Cl.[4] ............... A61B 17/06; A61B 17/28
[52] U.S. Cl. .................... 128/340; 128/321; 128/322; 81/383.5; 81/349
[58] Field of Search ............ 128/321, 340, 322; 81/383.5, 349

[56] References Cited

U.S. PATENT DOCUMENTS

| | | | |
|---|---|---|---|
| 1,498,488 | 6/1924 | Stallings | 81/309 |
| 1,659,112 | 2/1928 | Littlejohn | 128/322 |
| 2,002,594 | 5/1935 | Wappler et al. | 128/303.15 |
| 2,363,334 | 11/1944 | Jones | 128/340 |
| 3,091,841 | 6/1963 | Wurzel | 81/349 |
| 3,273,238 | 9/1966 | Kuhbier | 81/383.5 |
| 3,585,985 | 6/1971 | Gould | 128/321 |
| 3,895,636 | 7/1975 | Schmidt | 128/321 |
| 4,028,971 | 6/1977 | Budrose | 81/383.5 |
| 4,043,343 | 8/1977 | Williams | 128/321 |
| 4,258,716 | 3/1981 | Sutherland | 128/321 |

FOREIGN PATENT DOCUMENTS

| | | | |
|---|---|---|---|
| 0627970 | 3/1936 | Fed. Rep. of Germany | 128/325 |
| 0881030 | 7/1949 | Fed. Rep. of Germany | 81/349 |

OTHER PUBLICATIONS

Instrument Bulletin from Padgett Instruments, Kansas City, Mo., 1976.

*Primary Examiner*—D. E. Gantz
*Assistant Examiner*—Lance Johnson
*Attorney, Agent, or Firm*—Roberts, Spiecens, and Cohen

[57] ABSTRACT

A surgical needle holder is provided in which the handle members are arranged in a plane at right angles to associated jaws which are operated by the handles. A camming arrangement is coupled between the handles and jaws to convert the movement of the handles in one plane to movement of the jaws in a second perpendicularly arranged plane. The needle holder is employed for suturing in surgical procedures and facilitates placement of the hand of the operator as well as the application of force in a rotary sense thereby.

18 Claims, 6 Drawing Figures

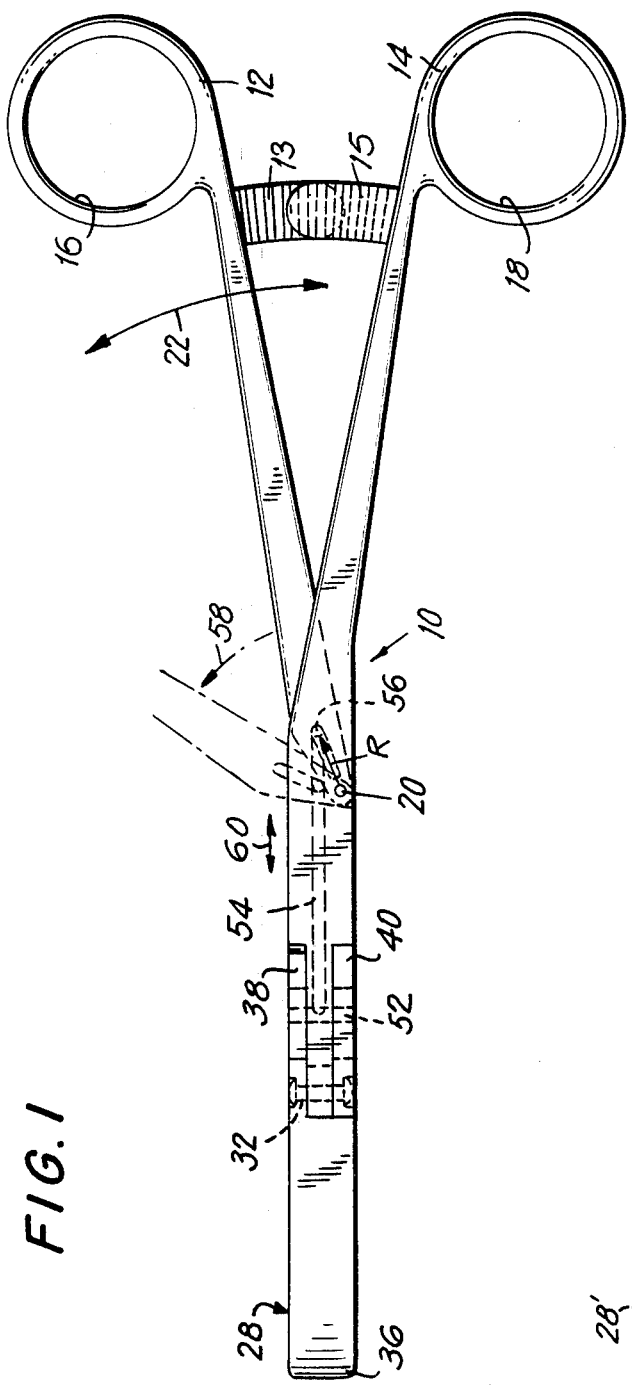
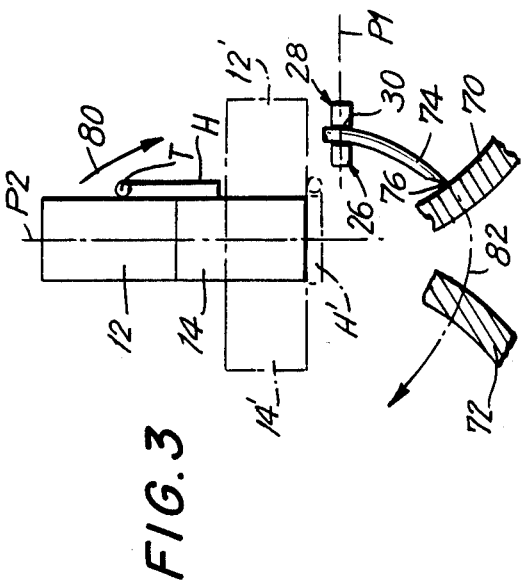
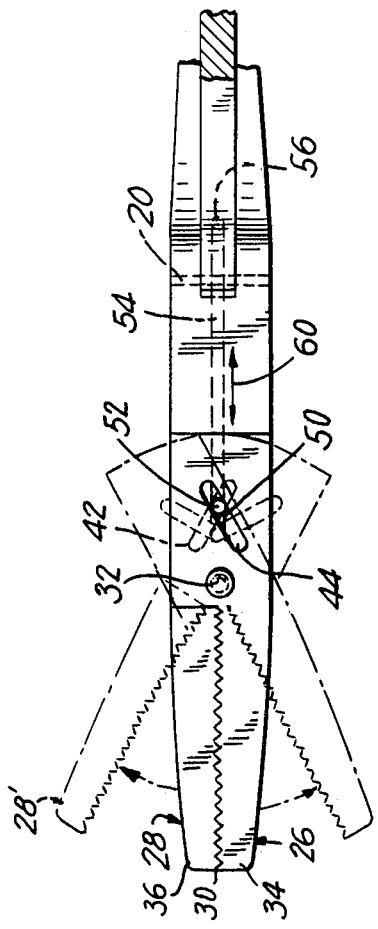

NONPLANAR SURGICAL NEEDLE HOLDER AND RELATED SUTURING METHOD

FIELD OF INVENTION

This invention relates to surgical instruments and more particularly to surgical needle holders of the type employed in connection with surgical suturing techniques. The invention also relates to surgical methods and, more particularly, to methods for improving hand position and the application of needle driving forces during suturing steps in surgical procedures.

BACKGROUND

There are a wider variety of surgical instruments involving the use of jaws or pincers or the like in which an instrument is provided with handles or provision is made for the relative movements of parts of the instrument involved. Some of these instruments are, by way of example, shown in U.S. Pat. Nos. 2,002,594; 3,585,985; 4,043,343; and 4,258,716.

In U.S. Pat. No. 2,002,594, R. H. Wappler et al show an instrument for electrical surgical treatment of tissue. In this instrument, a pair of handle members are arranged relative to a pivot with a pair of jaws being laterally offset relative thereto. As will be shown, this instrument is distinguishable from the type of instrument contemplated within the scope of the present invention because the pivot provided for the jaws is, in essence, arranged in parallel to the pivot provided for the handle members.

W. Gould shows in U.S. Pat. No. 3,585,985 a surgical instrument comprising a first assembly member having a handle portion, a shank portion and a tip portion all relatively fixed in spatial and structural relationship to each other. A second handle member is provided which is hingedly connected to the first assembly member at the juncture of the handle and shank portions. A shank member is provided which is hingedly connected to the second handle member which slidably mates with the shank portion of the first assembly member and a tip member hingedly connected to the shank member at the end thereof remote from the handle-shank hinge. It will be noted that in this instrument, the pivots provided for the handle members are parallel to the pivot provided for the shank.

In U.S. Pat. No. 4,043,343 (R. Williams), there is shown a forceps having a pair of handles, one of which is hinged for reciprocal movement relative to the other. Extension arms are provided between the handles. One of the arms is reciprocally slidable along the other arm. Upper and lower jaw members are furthermore provided, one of which is hinged for reciprocal movement relative to the other in response to reciprocal handle movement. In this arrangement, as in the above arrangement, the various pivots are provided in relative parallel attitude.

G. Sutherland shows, in U.S. Pat. No. 4,258,716, a microsurgical instrument having a handle adapted to be grasped by a surgeon and operating means being provided on the handle. An instrument body extends outwardly from the handle and has at its outer end the operative portion of the instrument which may, for example, be a scissors or forceps. The arrangement is such that the instrument body can be freely rotated about the axis of the handle to align the instrument in the required position with the body being located frictionally in position when the operating means is actuated. Thus, there is no firm predetermined position between the handle and instrument body as is necessary during certain types of procedures.

As will be shown hereinafter, the present invention provides for a relative arrangement of handles and jaws. Since the conception of the present invention, I have researched the various prior art and find that there are non-surgical instruments which provide, in general, a type of relative placement of parts of the type with which I am generally concerned. Some of these relationships are shown in U.S. Pat. Nos. 2,679,096; 3,296,697; 3,325,896; and 3,375,581. In these previously granted patents are shown grass shears in which handles relatively pivotable in one plane are related to cutting blades which are relatively pivotal in a second plane which is perpendicular to the first plane. As will become apparent hereinafter, I employ an arrangement with a camming construction which is different from anything shown in the above patents while at the same time, I employ the arrangement of the jaw plane and handle plane for a purpose and in a manner heretofore unrecognized.

SUMMARY OF INVENTION

It is an object of the invention to provide an improved surgical instrument and particularly a surgical instrument suitable to constitute a surgical needle holder of improved characteristics.

As will be shown hereinafter, there is provided in accordance with the invention a needle holder in which the jaws function in a plane perpendicular to the plane in which the handle members pivot. By having the jaws of the apparatus in a perpendicular plane, the related needle which is grasped is in a position to function while the operator's hand is in a neutral position. The advantages of this is multifold. Firstly, the needle is in a position to enter the tissue without any hand motion. In other words, the hand does not have to be cocked to an unnatural position. Secondly, the motion required to place and bury the needle in the tissue being sewn is substantially reduced due to the starting angle of the needle. Moreover, the needle is moved by a more natural motion of the hand of the operator doing the suturing. Thirdly, the needle can be readily removed from the tissue without cocking the wrist or twisting the needle holder.

In achieving the above and other objects and advantages of the invention, there is provided a surgical needle holder comprising first and second handle members and first and second jaw members cooperatively associated to constitute a means for grasping and manipulating a surgical needle. A coupling means is provided which couples the jaw and handle members so that the jaw members are relatively pivotable about a first pivot axis which is angularly disposed to a second pivot axis on which the handle members are relatively pivoted and so that the jaw members pivot relative to each other in response to a relative pivoting of said handle members.

According to a specific embodiment of the invention, the first pivot axis is at least generally perpendicular to the second pivot axis. It is possible, in accordance with the invention, that this angle be other than perpendicular, although the perpendicular arrangement constitutes the preferred and most useful embodiment of the invention, according to the present analysis thereof.

According to a first embodiment of the invention, one of the jaw members is an extension of and monolithic with one of the handle members. According to a second embodiment, the jaw members are not monolithic with the handle members at all. Moreover, enterengaging means are respectively mounted on the handle members for releasably locking the handle members together and thereby locking the jaw members in fixed relative positions. These enterengaging means may be relatively planar ratchet members or the like.

In accordance with the invention, the jaws members are provided with intersecting slots which are in superposed relationship. An intervening guide member may additionally be employed. The coupling means, as will be seen, includes a camming member simultaneously accommodated in both of these slots whereby to effect a pivoting of the jaw members. The coupling means, moreover, includes a rod coupled between the camming member and the other of the handle members. This rod translates movement of the handle member to which it is coupled into movement of the camming member in the aforesaid slots. Special constructions of the handle members are also envisaged.

In accordance with yet another aspect of the invention, the coupling means mentioned above includes a first pivot coupling the handle members together and a second pivot on the other handle member and radially spaced from the first pivot, said second pivot coupling said rod to said other handle member whereby displacement of said other handle member displaces said rod and thereby said camming member.

The aforesaid construction is related to jaw members which conventionally have relatively flat surfaces adapted to oppose each other in face-to-face relationship and which furthermore are adapted for relative movements in directions generally perpendicular to the flat surfaces.

The invention also relates to a method of surgical suturing pertaining to the above wherein a curved needle is employed to sew together the edges of two tissue sections. The method comprises grasping the needle in a needle holder having jaws arranged, as mentioned above, such that the jaws are arranged to cooperate along a plane with handles being coupled to the jaws and operable in a plane to open and close the aforesaid jaws. In accordance with the invention, the method comprises arranging the planes at an angle relative to each other whereby to facilitate grasping said handles in the hand of a suturer and operating the aforenoted needle.

As has been indicated above, the planes are perferably arranged to be perpendicular with respect to each other. In association with the aforegoing. The holder will be displaced with a rotary motion to exchange positions of the planes.

In accordance with a preferred aspect of the method of the invention referred to generally hereinabove, the plane of the handles is initially in generally vertical attitude whereby the hand of the suturer is also initially in generally vertical attitude. From this arrangement, the needle is driven in a generally arcuate path through the edges of the tissue section by rotary motion of the needle holder.

The above and further objects and advantages as well as features of the invention will be explained in greater detail hereinbelow with reference to the accompanying drawing.

BRIEF DESCRIPTION OF DRAWING

In the drawing:

FIG. 1 is a side view of a surgical needle holder provided in accordance with a preferred embodiment of the invention;

FIG. 2 is a top view of the tip or jaw section of the surgical instrument of FIG. 1;

FIG. 3 is a diagrammatic illustration of the application of the method of the invention according to one aspect thereof;

DETAILED DESCRIPTION

Figure 5:
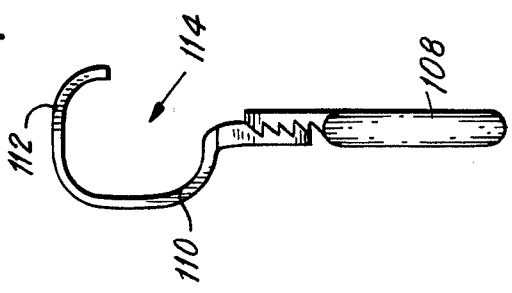
FIG. 5 is a rear view of the structure of FIG. 4.

In FIGS. 1 and 2 is shown a surgical instrument 10 having handle members 12 and 14 having openings 16 and 18 therein for receipt of respective fingers on the applied hand of the operator in a surgical procedure. The instrument will be employed to grasp a surgical needle, as will be shown in greater detail hereinafter. The instrument is adapted to be grasped by the hand of the suturer which hand is the hand most normally employed by the user (i.e., the right hand of a right-handed person).

The handle members 12 and 14 are pivoted together about a pivot pin indicated at 20. This enables the handle members to partake in a relative pivotal movement in a plane such as, for example, the plane of FIG. 1 of the drawing. This movement is indicated by arrow 22. The movement is reciprocal, i.e. in one instance the members move relatively towards one another and in another instance the handle members move relatively away from one another.

The surgical instrument 10 furthermore comprises jaw members 26 and 28. These jaw members meet and cooperate against a pair of facing surfaces indicated at 30. These surfaces are slightly serrated. These surfaces are the surfaces which grasp the needle therebetween for purposes of manipulation as will be shown in greater detail hereinbelow.

The jaw members are capable of a reciprocal movement about a pivot 32. In other words, the jaw members can move towards and/or away from one another. They do this in a plane which is perpendicular to the drawing in FIG. 1 and parallel with the plane of the drawing as seen in FIG. 2. The jaw members have sections (i.e. sections 34 and 36 which oppose each other and sections 38 and 40 which overlap each other).

In sections 38 and 40, are provided respective rectilinear slots 42 and 44 which cross each other in the nature of an X. The slots are superposed relative to one another and include a section 50 in which the slots cooperatively pass entirely through the jaw section. In section 50 is accommodated a camming member 52, the motion of which, in a manner to be described hereinafter, affects an opening and closing of the jaw sections relative to one another. Thus, for example, the jaw section 28 may be moved to a position indicated in chain line at 28'.

The cam or camming member 52 is, in effect, an elongated cylindrical member such as a pin. It is attached to a rod 54 in turn connected to a pivot pin 56 mounted on the handle member 12. The pivot pin 56 is radially spaced from pivot pin 20 by an amount indicated at R. The pin 56 is, therefore, displaceable about pin 20 in the direction indicated by arrow 58. This movement, in turn occasioned by displacement by handle member 12 relative to handle member 14 in the direction indicated by arrow 22, effects a displacement of rod 54 as indicated by arrow 60. This, in turn, effects a displacement of camming member 52 to alter the angular attitude of the slots 42 and 44 to bring about a relative displacement of the jaw members 28 and 30. Thus, there will be seen that a relative movement of the handle members 12 and 14 is converted to a relative movement of the jaw members 28 and 30 with the respective relative movements taking place in planes which are angularly related and preferably perpendicular with respect to one another.

Utilization of the aforegoing instrument and its characteristic movements is illustrated in one form thereof in FIG. 3. Therein are shown the edge portions 70 and 72 of two tissue sections which are to be sewn together in a suturing procedure which is part of a surgical operation. The needle is shown at 74. It is a conventional curved surgical needle having a point indicated at 76. It is preferably grasped between jaw members 26 and 28 with these members occupying a horizontal plane. The plane along which the jaw members 26 and 28 cooperate is indicated in vertical attitude at 30.

The handle members 12 and 14 are indicated in FIG. 3 as being in a vertical plane and operatively displaceable parallel thereto. The hand of the operator is indicated at H with the thumb indicated at T. It will thus be seen that the hand of the operator occupies a vertical position parallel to the plane of handle members 12 and 14 and to the plane in which they are relatively displaceable.

From the above description, it will be appreciated that the hand of the operator as well as the plane of jaw members 12 and 14 is perpendicular to that of the members 26 and 28. For purposes of elucidation the plane of the jaw members 26 and 28 is indicated at P1 and the plane of the handle members 12 and 14 is indicated at P2. Thereafter, the hand is rotated in the direction indicated by arrow 80 to assume the position indicated at H'. This carries with it the handle members 12 and 14 which move to the positions indicated at 12' and 14'.

By this motion the surgical needle 74 is driven first through tissue section 70 and then through tissue section 72 or the edges thereof in the direction indicated by the dotted line at 82 and therefore the suturing operation or a portion thereof takes place.

From the above it will be seen that a method of surgical suturing is provided wherein a curved needle is employed to sew together the edges of two tissue sections or the like. This method comprises grasping the needle in a needle holder having jaws arranged to cooperate along a plane and handles coupled to the jaws and operable in a plane to open and close these jaws. In accordance with the invention the method comprises arranging said planes at an angle relative to each other whereby to facilitate grasping of the handle in the hand of a suturer. By visualization and reference to FIG. 3, it can be seen that the initial grasping position is a conventional position in which the palm or back of the hand is vertical and the hand is in a natural position uncocked and with no torsional stresses or other muscular or ligament pressures applied thereto. From this position, the hand can be readily rotated in a clockwise direction as visualized with reference to FIG. 3 with the motion being quite normal and a maximum of pressure being enabled without bringing any distortional contractions to the hand being employed.

As stated above, the invention is preferably such that the planes are arranged perpendicularly of each other. The holder is displaced with a rotary motion as aforesaid to exchange positions of the planes. In the initial condition, the plane of the handles is preferably generally of vertical attitude whereby the hand of the suturer is also, as stated above, initially in generally vertical disposition. The needle is driven along a generally arcuate plane through the edges of the tissue sections by the rotary motion of the hand of the operator and of the holder.

In the construction which has been described above, one of the jaw members (i.e. jaw member 26) is a continuation of and monolithic with the handle member 14. Other constructional arrangements are possible within the scope of the invention if certain advantageous characteristic features of the invention are to be disregarded.

Figure 4:
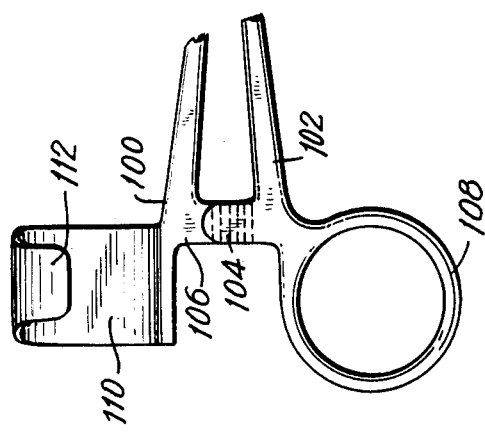
FIG. 4 illustrates a variation of the handle portion of the holder of FIGS. 1-3.

With reference to FIGS. 4 and 5, it is seen that a variation in the handle members is contemplated in the scope of the invention. In FIGS. 4 and 5 are shown handle members 100 and 102. Ratchet members 104 and 106 extend between the handle members for purposes of locking the same in position in the manner which was discussed hereinabove. Handle member 102 is seen as including a finger ring support 108 of conventional design. Handle member 100 carries a hooked shaped configuration 110 having a curved flange 112 which cooperatively defines an open throat 114 for purposes of providing an open access for the thumb of the user. Thus, it will be readily appreciated that the thumb of the user can be readily inserted and withdrawn from the opening defined by the hooked shaped configuration 110. It is to be noted that by eliminating the top ring, comfort for the user is substantially increased. Furthermore, there is no room for the thumb to get caught in the top ring. Moreover, the palming of the instrument is facilitated with substantially greater control.

Figure 6:
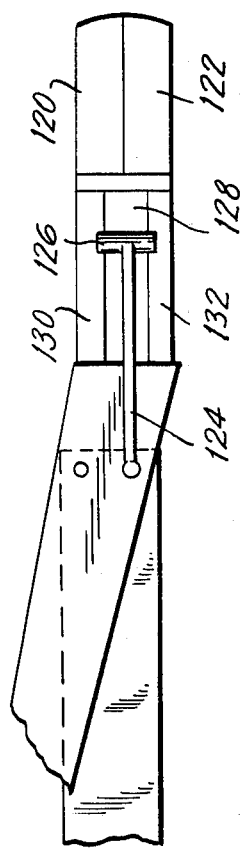
FIG. 6 shows a variation of the camming action in FIGS. 1-3.

FIG. 6 illustrates a variation in the camming control. In FIG. 6 are shown jaw members 120 and 122. A control rod 124 is seen which is similar to the control rod noted hereinabove. It controls displacement of the camming member 126. In this embodiment of the invention, there is provided an intervening guide member 128 provided with a slot through which extends the camming member 126. This intervening guide member 128 may be rigid with one of the handle members. It is in intervening relationship between portions 130 and 132 of jaw members 120 and 122. In this embodiment of the invention, no directly monolithic connection between the jaw members and any one of the handle members is employed.

There will now be obvious to those skilled in the art, many modifications and variations of the structure and methods set forth hereinabove. These modifications and variations will not depart from the scope of the invention if defined by the following claims.

What is claimed is:

1. A surgical needle holder comprising first and second handle members in a first plane, first and second jaw members cooperatively associated in a second plane to constitute means for grasping and manipulating a surgical needle, and coupling means coupling said jaw and handle members so that the jaw members are relatively pivotal about a first pivot axis which is angularly disposed to a second pivot axis on which the handle members are relatively pivotal and so that the jaw members pivot relative to each other in response to a relative pivoting of said handle members, said jaw members and handle members being related to each other such that, when said first plane is vertical, said second plane is at least substantially horizontal.

2. A surgical needle holder as claimed in claim 1 wherein the first pivot axis is at least generally perpendicular to and spaced from the second pivot axis.

3. A surgical needle holder as claimed in claim 2 wherein one of the handle members include an extension and the jaw members are supported on the extension of said one handle member.

4. A surgical needle holder as claimed in claim 3 wherein interengaging means are respectively mounted on said handle members for releasably locking the handle members and thereby the jaw members in fixed relative positions.

5. A surgical needle holder as claimed in claim 4 wherein the interengaging means are relatively planar ratchet members.

6. A surgical needle holder as claimed in claim 3 wherein the jaw members are provided with intersecting slots in superposed relationship and said coupling means includes a camming member simultaneously accommodated in both said slots whereby to effect a pivoting of said jaw members.

7. A surgical needle holder as claimed in claim 6 wherein said coupling means includes a rod coupled between said camming member and the other of said handle members.

8. A surgical needle holder as claimed in claim 7 wherein said coupling means includes a first pivot coupling said handle members together and a second pivot on said other handle member and radially spaced from said first pivot said second pivot coupling said rod to said other handle member whereby displacement of said other handle member displaces said rod and thereby said camming member.

9. A surgical needle holder as claimed in claim 8 wherein said jaw members have relatively flat surfaces adapted to oppose each other in face-to-face relationship and adapted for relative movement in directions generally perpendicular to the flat surfaces.

10. A surgical needle holder as claimed in claim 3 wherein one of said jaw members is monolithic with one of said handle members.

11. A surgical needle holder as claimed in claim 3 comprising a guide member intervening between said jaw members.

12. A surgical needle holder as claimed in claim 11 wherein the jaw members are provided with intersecting slots in superposed relationship and said coupling means includes a camming member simultaneously accommodated in both said slots whereby to effect a pivoting of said jaw members; said guide member also being provided with a slot in which said camming member is guided.

13. A surgical needle holder as claimed in claim 1 wherein one of said handle members includes a finger ring and the other of said handle members includes a hooked shaped configuration defining an open access for the thumb of a user.

14. A method of surgical suturing wherein a curved needle is employed to sew together the edges of two tissue sections, said method comprising grasping said needle in a needle holder having jaws arranged to cooperate along a plane and handles coupled to the jaws and operable in a plane to open and close said jaws, said method further comprising arranging said planes at an angle relative to each other whereby to facilitate grasping said handles in a hand of a suturer and such that, when the handles are in a vertical plane, the jaws are parallel to a plane which is at least substantially horizontal.

15. A method as claimed in claim 14 wherein the planes are arranged perpendicularly of each other.

16. A method as claimed in claim 15 comprising displacing the holder with a rotary motion to exchange positions of the planes.

17. A method as claimed in claim 16 wherein the plane of the handles is initially in generally vertical attitude whereby the hand of the suturer is also initially in generally vertical attitude.

18. A method as claimed in claim 16 comprising driving the needle along a generally arcuate path through the edges of the tissue sections by the rotary motion of the holder.

* * * * *